United States Patent [19]
Cole

[11] Patent Number: 5,512,158
[45] Date of Patent: Apr. 30, 1996

[54] CAPILLARY ELECTROPHORESIS METHOD AND APPARATUS FOR ELECTRIC FIELD UNIFORMITY AND MINIMAL DISPERSION OF SAMPLE FRACTIONS

[75] Inventor: Wesley D. Cole, Palo Alto, Calif.

[73] Assignee: Hewlett-Packard Company, Palo Alto, Calif.

[21] Appl. No.: 395,268

[22] Filed: Feb. 28, 1995

[51] Int. Cl.⁶ .................. G01N 27/26; G01N 27/447
[52] U.S. Cl. .................. 204/453; 204/455; 204/459; 204/604; 204/605; 204/610
[58] Field of Search .................. 204/299 R, 182.8, 204/180.1

[56] References Cited

U.S. PATENT DOCUMENTS

| | | | |
|---|---|---|---|
| 5,290,587 | 3/1994 | Young et al. | 427/122 |
| 5,296,116 | 3/1994 | Guttman | 204/180.1 |
| 5,324,413 | 6/1994 | Gordon | 204/299 R |

OTHER PUBLICATIONS

Sandra Sloss and Andrew G. Ewing "Improved Method for End–Column Amperometric Detection for Capillary Electrophoresis" Analytical Chemistry, vol. 65, No. 5 (Mar. 1, 1993) 577–581.

Primary Examiner—John Niebling
Assistant Examiner—John S. Starsiak, Jr.

[57] ABSTRACT

A capillary electrophoresis method and apparatus for reducing dispersion of sample fractions are disclosed. The capillary tube in which the electrophoresis is performed has been flared, at least at its sample entrance end, to remove sharp corners which contribute to aberrations in the electric field distribution in a radial direction and result in differential migration of molecules depending on their proximity to the sharp corners. The flared tube, in contrast to a conventional tube, provides a more uniform electric field for electrophoresis and reduces undesired dispersion of the samples.

17 Claims, 2 Drawing Sheets

CAPILLARY ELECTROPHORESIS METHOD AND APPARATUS FOR ELECTRIC FIELD UNIFORMITY AND MINIMAL DISPERSION OF SAMPLE FRACTIONS

DESCRIPTION

1. Technical Field

The invention relates to devices and techniques for electrophoretic separation of samples.

2. Background Art

Applications for electrophoresis, an analytical technique for separating biologically important molecules in a sample, include determining a sample's homogeneity, determining molecular weights of proteins and nucleic acids, mapping nucleic acid primary structures, i.e. DNA and RNA sequence analyses, and defining phenotypic variance of protein at the molecular level. Electrophoretic techniques rely on the fact that each molecular species has a unique combination of mass, size, shape, charge, density, and sub-unit structure, with the unique combination creating mobility differences responsive to an electric field. Various electrophoretic techniques use one or more of these properties to cause varying degrees of molecular separation via the migration of the molecular species under a constant or varying electric field.

Capillary electrophoresis is a technique using a capillary tube which is filled with a separation matrix, such as a gel or buffer fluid. A small amount of sample is introduced into one end of the capillary tube and a potential difference is applied along the tube. Differences in the electrophoretic mobilities of different molecules cause the fractions of the sample to emerge separated at the outlet end of the capillary tube. Migration of the various fractions as sharp bands and their emergence over a relatively short, clearly defined time is desirable for separation and later identification purposes. If, on the contrary, sample constituents are widely dispersed in the capillary tube, the constituents are difficult to identify and quantify.

Establishing the proper electric field is one requirement for achieving an accurate analysis of a sample. The potential difference applied along the capillary tube creates an electric field along the longitudinal axis of the tube. For example, a capillary tube having a length of 25 cm will have an electric field magnitude of 200 V/cm when a potential difference of 5 kV is applied along the capillary tube. Varying the longitudinal electric field will vary the migration rate of sample constituents, or fractions.

In addition to the longitudinal electric field, there is also a radially extending electric field. A charge accumulation at the interior tube surface results from preferential adsorption of anions from the buffer solution that fills the migration path of the capillary tube. The negative charge of the anions attracts a thin layer of mobile positively charged buffer ions. The radially-oriented electric potential is referred to as "zeta potential."

One potential effect of a nonuniform electric field distribution across a capillary tube is that individual molecules of a particular sample constituent may be accelerated at different rates. Variations in acceleration broaden the constituent bands of a sample, thereby decreasing the separation efficiency of the process. This may be particularly troublesome in the capillary volume context, since samples are often obtained in very limited volumes and are often subjected to other experimental processes before the electrophoretic separation. Electrophoretic dispersion of the sample constituents hinders their analysis, and may even lead to loss of the sample.

U.S. Pat. No. 5,290,587 to Young et al., which is assigned to the assignee of the present invention, describes a method of making a capillary tube so as to decrease the susceptibility of the tube to electrical nonuniformities. A resistive coating is formed along the exterior of the capillary tube. The resistivity of the coating is uniform along the length of the coating, so that a generally uniform electric field is created by the application of a potential difference to the coating. The externally applied potential difference is vectorially coupled to the longitudinal electric field along the migration path of the tube in a manner to achieve a desired zeta potential. The Young et al. method of fabricating the capillary tube may be used to increase the accuracy of an electrophoretic separation. However, other improvements may further enhance accuracy.

What is needed is a method and system for enhancing uniformity of electric field distribution in capillary electrophoresis.

SUMMARY OF THE INVENTION

The invention is a method and apparatus in which a capillary tube is formed so as to provide a smoothed contour at the end of the tube, at least with respect to the transition from the interior surface of the tube to the end of the tube. Material is removed from the entrance end portion of the tube, as by chemical etching, so that sharp edges to the interior surface are removed. In the preferred embodiment, the removal of material provides an entrance end portion in which the inside diameter of the tube increases with approach to the end of the tube.

By modeling the electric field distribution in a capillary tube during a capillary electrophoresis separation, it has been discovered that the shape of the end portions significantly affects the distribution. When a potential difference is applied along a conventional capillary tube, sharp corners at the end portions tend to define differences in electric field concentrations. Because of the nonuniformity at the end portions, ions moving past the ends may undergo different accelerations depending upon the positions of the ions relative to the central axis of the capillary tube. Consequently, dispersion of a sample during insertion into the tube may be increased, adversely affecting the overall separation efficiency of the process. "Separation" of samples is the desired result of electrophoresis, causing fractionation of a sample of mixed components. "Dispersion," however, refers to the scattering of molecules of a component, and is usually not a desired consequence of the technique. The adverse effects are multiplied for applications in which capillary tubes are joined together, since each conventionally formed capillary tube will define its own electric field concentrations.

By smoothing the contour of the entrance end portion of a capillary tube in accordance with the present invention, the dispersion of a sample during insertion is reduced. In the preferred embodiment, material is also removed at the exit end portion in order to smooth the transition from the interior to an end surface at the exit. If capillary tubes are to be joined together, each tube is treated at both ends in order to provide the smooth contour.

In operation, the entrance and exit end portions are inserted into separate buffer reservoirs. Electrodes are used to apply a potential difference along the capillary tube in order to initiate electrophoretic separation. The removal of the sharp edges at the end portions results in a capillary tube that is flared at the end portions of its bore and provides a uniformity of the electric field distribution in a radial direction. The smooth contour may be achieved by a chemical etching process using hydrogen fluoride, but other techniques may be employed.

An advantage of the invention is that sample dispersion is reduced, i.e. the bands of sample fractions separated during the electrophoretic process are narrower, facilitating identification and quantification of the fractions.

BEST MODE FOR CARRYING OUT THE INVENTION

Figure 1:
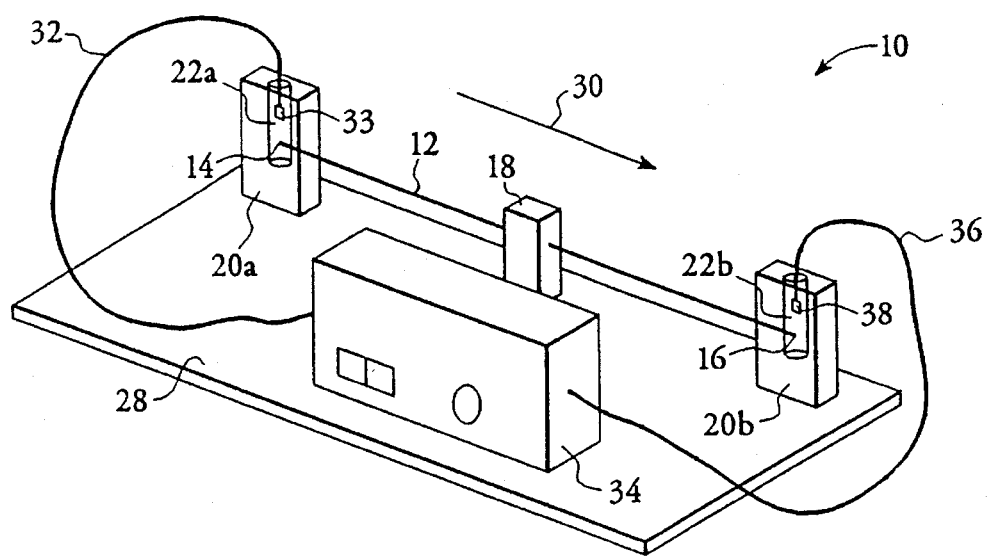
FIG. 1 shows a conventional capillary electrophoresis apparatus.

With reference to FIG. 1, a conventional electrophoretic system 10 is shown as including a capillary tube 12 having an entrance end 14 and an exit end 16. The capillary tube is of the type known in the art. The capillary tube may be a fused silica member having an inside diameter of 50 microns and having an outside diameter that is in the range of 140 microns to 500 microns, but these dimensions are not critical.

An on-column detector 18 is located along the length of the capillary tube 12. Ultraviolet absorbance, fluorescence, chemiluminescence, refractive index, or conductivity detectors are generally used. The optical coupling of the detector to the capillary tube permits detection of movement within the capillary tube.

The entrance end 14 of the capillary tube 12 is inserted into a buffer reservoir 22a. At the opposite side of the detector 18, exit 16 of tube 12 is inserted into a buffer reservoir 22b. The buffer reservoirs 22a–b are in fluid communication with the contents of tube 12. Reservoirs 22a–b are shown within holders 20a–b, respectively. The two holders 20a–b and detector 18 are shown as resting on a table 28.

A high voltage power supply 34 is connected to the reservoirs 22a–b. A first lead line 32 is used to apply a first electrode 33 to reservoir 22a. In the same manner, a second lead line 36 applies a second electrode 38 to reservoir 22b. Power supply 34 provides a potential difference between the ends of tube 12. The migration of the electrophoresed sample will be along arrow 30, i.e. from entrance 14 of tube 12 toward exit 16. The fractions of the sample separate along the length of tube 12 according to one or more of the following: charge, mass, size, shape, density, and sub-unit structure.

Figure 2:
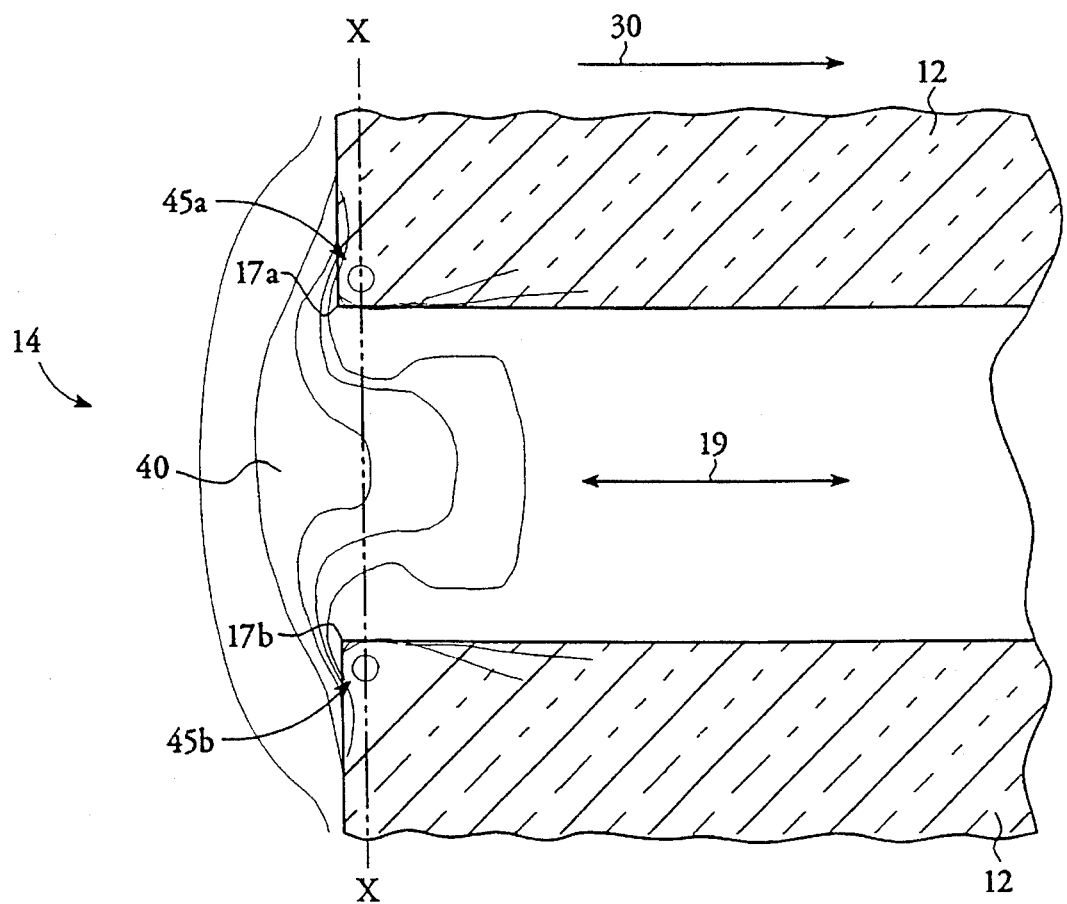
FIG. 2 shows the electrical field distribution at the end of a conventional capillary tube.

FIG. 2 shows an end portion of a conventional capillary tube 12 in longitudinal cross-section and also shows the electric field distribution at entrance 14. The electric field magnitude is visible as lines 40 and region 45a–b. Each line is representative of a constant electric field magnitude. A sharp corner, shown at 17a–b, exists at the inside diameter of tube 12, because of the way in which tube 12 is prepared for usage. Typically, the capillary tube is cut or otherwise segmented from a larger length of tubing, producing end surfaces that are generally perpendicular to the interior and exterior surfaces of the tube.

The electric field that results upon application of a potential difference along tube 12 is nonuniform in a radial direction, having a region of especially high magnitude 45a–b at the corner 17a–b of tube 12. This nonuniformity causes differential separation of identical molecules, depending upon the proximity of the identical molecules to either the sharp corner 17a–b or the central axis 19 of tube 12. For instance, at the plane x represented in FIG. 2 by line x-x, the molecules will travel at different rates according to their locations in the plane because of the extremely variable electric field magnitudes present in a radial direction. Plane x crosses many lines of constant electric field magnitude, thus signifying nonuniform electric field magnitude along the plane. This aberration in the separation process contributes to dispersion of the sample fractions.

Figure 3:
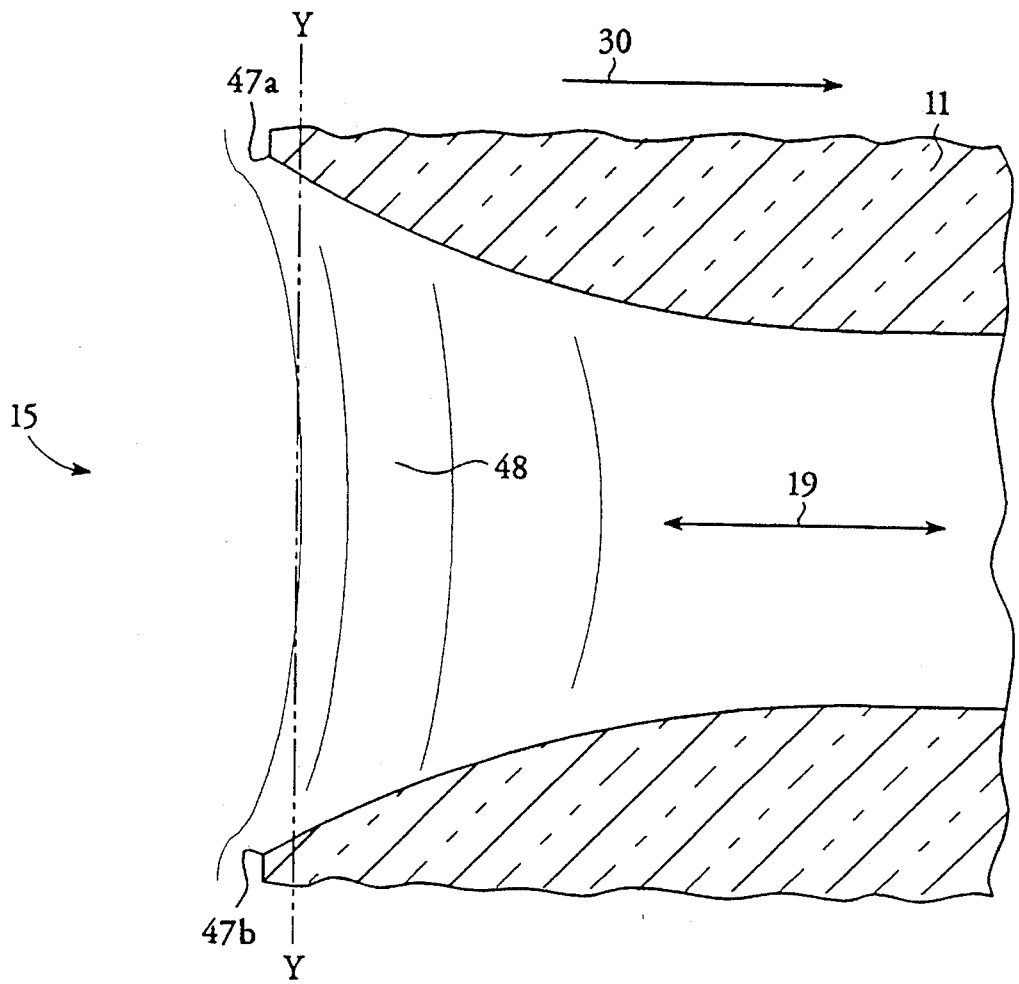
FIG. 3 shows the electrical field distribution at the end of a flared capillary tube, according to the present invention.

FIG. 3 presents a flared capillary tube 11, in accordance with the present invention. The interior of tube 11 is treated so as to remove its sharp edge at the entrance end or terminus and to smoothly contour its surface. Chemical etching with hydrogen fluoride is the preferred method of shaping tube 11, but other techniques may be utilized, as will be appreciated by persons skilled in the art. The resulting entrance opening 15 of tube 11 is flared, or trumpet-shaped, preferably with an interior surface at an obtuse angle to the end surface, as illustrated at 47a–b of FIG. 3. Tube 11 is preferably not flared drastically to its exterior edges, as that may cause breakage and create new sharp corners. A flare ending in an internal diameter in the range of two to three times the original internal diameter of the tube is preferred. The shape of tube 11 represents a compromise between the mechanical considerations of capillary electrophoresis, wherein a uniform internal diameter is preferred, and the electrical considerations, wherein sharp edges should be removed. The direction of sample migration in tube 11, as with tube 12, is along arrow 30.

The electric field 48 that is obtained through the use of flared tube 11 is more uniform. To illustrate, line y-y of FIG. 3, representing plane y and incorporating the diameter of tube 11 at the position of line y-y, does not cross many electric field magnitude lines, which indicates the electric field distribution is relatively uniform in a radial direction along plane y. Therefore, a sample that undergoes electrophoresis in a system according to the present invention is less likely to be dispersed at the entrance and its fractions are more likely to migrate as sharp, recognizable bands. The tube 11 may be incorporated into an electrophoretic system as by substituting flared tube 11 for sharp-cornered tube 12 in the system 10, presented in FIG. 1. The teachings of the present invention are also applicable in a larger format, such as electrophoresis in a large-sized tube or lane.

Figure 4:
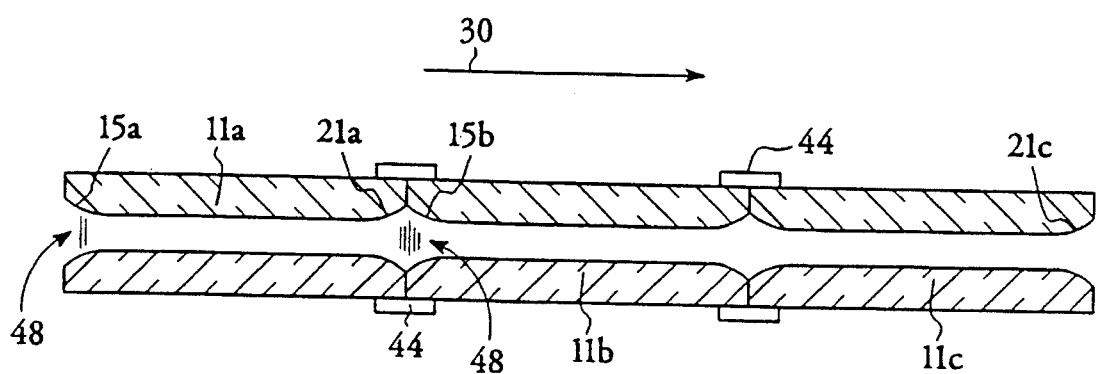
FIG. 4 shows aligned flared capillary tubes, according to the present invention.

Tube 11 may be similarly flared at its exit end, opposite entrance 15, so that the electric field remains uniform in the exit region, instead of being influenced by the sharp corner of the exit end. This is important if the sample will be electrophoresed up to the exit region, e.g. if detector 18 is positioned near the exit region, or if the sample fractions are to be collected from the exit end of tube 11 or are to pass through to other similar tubes that have been joined to tube 11. In FIG. 4, multiple flared tubes 11a–c are shown. Each tube is flared at both its entrance end 15 and its exit end 21. Tubes 11a–c are aligned axially, i.e. in an end-to-end format. They are then butted together and joined, as with couplers 44. The sample to be fractionated is introduced at entrance 15a of tube 11a and electrophoresis proceeds toward exit 21c of tube 11c in direction 30, as before. In the previous practice, when capillary tubes were axially-aligned for electrophoresis, the electrical field was non-uniform because of the sharp corners where the tubes were joined.

The present invention provides an effective method of improving electrophoretic separation efficiency providing an advance in the analysis of small-volume and sometimes difficult-to-obtain samples.

While perhaps the invention adapts most easily to use in capillary zone or capillary gel electrophoresis, the invention may be used with other electrophoretic techniques in which a capillary tube is employed. For example, the invention may be used with capillary isoelectric focusing, which employs separation of sample constituents by isoelectric point in a pH gradient formed over the length of the capillary.

I claim:

1. A method of forming a capillary tube for use in capillary electrophoresis comprising:

selecting an entrance end portion of said capillary tube, said entrance end portion having an inside diameter, interior and exterior surface, and an end surface that is generally perpendicular to said interior and exterior surfaces;

removing material from said interior surface of said entrance end portion such that said entrance end portion has a smooth contour with an increasing inside diameter with approach to said end surface; and removing material at an exit end portion of said capillary tube such that a smooth contour is defined from said interior surface to a second end surface opposite to said end surface of said entrance end portion.

2. The method of claim 1 wherein removing said material is a step of removing material at the inside diameter of said capillary tube such that said interior surface is at an obtuse angle to said end surface.

3. The method of claim 1 wherein removing said material is a step of removing material at the inside diameter of said capillary tube such that the inside diameter at said end surface is increased by an amount in the range of two to three times.

4. The method of claim 1 wherein removing said material includes chemically etching said entrance end portion.

5. The method of claim 1 further comprising connecting said exit end portion to a second capillary tube having a similar contour.

6. A method for reducing dispersion of sample fractions during capillary electrophoresis, the method comprising:

providing a capillary tube with an entrance end, an exit end, and an internal diameter;

flaring the interior of the tube at the entrance end of the tube to remove sharp edges;

inserting a separation matrix into the tube;

inserting a sample for separation into the tube at the entrance end, the sample having electrically charged fractions;

placing each end of the tube in a buffer reservoir;

introducing an electrode into each buffer reservoir; and applying an electric potential to the tube through the electrodes to create an electric field, the direction of the field being adjusted such that the sample will travel from the entrance end through the tube;

whereby the electric field is relatively uniform proximate to the entrance end.

7. The method of claim 6 wherein flaring the interior comprises etching the interior of the tube with a chemical.

8. The method of claim 7 wherein etching the interior with a chemical comprises treating the interior of the tube with hydrogen fluoride.

9. The method of claim 6 wherein flaring the interior comprises flaring so that the internal diameter of the tube is increased by an amount in the range of two to three times at the entrance end.

10. The method of claim 6 further comprising flaring the interior of the tube at the exit end of the tube to remove sharp edges.

11. The method of claim 10 further comprising aligning and coupling multiple tubes having flared entrance and exit ends in an end-to-end format such that the sample may be passed through the coupled tubes, whereby the electric field is relatively uniform throughout the coupled tubes.

12. An electrophoretic system for reducing dispersion of sample fractions, the system comprising:

a tube having an internal diameter, an entrance end and an exit end, the tube being flared at an interior at the entrance end, the interior having a smooth contour at a terminus of said entrance end;

at least two buffer reservoirs, each reservoir holding one of the entrance and exit ends of the tube; and at least two electrodes, each electrode positioned substantially external to said tube in one of the reservoirs and connected to a source of electrical power to cause an electric field to pass a sample introduced at the entrance end of the tube toward the exit end of the tube.

13. The electrophoretic system of claim 12 wherein the tube is flared so that its internal diameter at said terminus is increased by an amount in the range of two to three times.

14. The electrophoretic system of claim 12 wherein the tube is flared at an interior at the exit end of the tube, the interior having a smooth contour at a terminus of said exit end.

15. The electrophoretic system of claim 14 further comprising multiple flared tubes aligned and coupled in an end-to-end format.

16. The electrophoretic system of claim 12 wherein the tube is flared by a chemical etching treatment with hydrogen fluoride.

17. An electrophoretic system for reducing dispersion of sample fractions, the system comprising:

a tube having an internal diameter, an entrance end and an exit end, the tube being flared at an interior at the entrance end and at the exit end, the interior having a smooth contour at a terminus of said entrance end;

at least two buffer reservoirs, each reservoir holding one of the entrance and exit ends of the tube; and at least two electrodes, each electrode positioned in one of the reservoirs and connected to a source of electrical power to cause an electric field to pass a sample introduced at the entrance end of the tube toward the exit end of the tube.

* * * * *